US012656290B2

(12) United States Patent
Kang

(10) Patent No.: US 12,656,290 B2
(45) Date of Patent: Jun. 16, 2026

(54) MICROSENSOR FOR MONITORING PHOSPHINE AND PREPARATION METHOD THEREOF

(71) Applicant: Sensix (Nanjing) Environmental Technology Co., Ltd., Nanjing (CN)

(72) Inventor: Fuxing Kang, Nanjing (CN)

(73) Assignee: Sensix (Nanjing) Environmental Technology Co., Ltd., Nanjing (CN)

( * ) Notice: Subject to any disclaimer, the term of this patent is extended or adjusted under 35 U.S.C. 154(b) by 251 days.

(21) Appl. No.: 18/347,411

(22) Filed: Jul. 5, 2023

(65) Prior Publication Data

US 2024/0019392 A1    Jan. 18, 2024

(30) Foreign Application Priority Data

Jul. 12, 2022    (CN) .......................... 202210818509.1

(51) Int. Cl.
G01N 27/30        (2006.01)
C03B 37/025      (2006.01)
        (Continued)

(52) U.S. Cl.
CPC ......... G01N 27/30 (2013.01); C03B 37/0256 (2013.01); C25D 3/48 (2013.01);
        (Continued)

(58) Field of Classification Search
CPC .. G01N 27/30; G01N 27/416; G01N 27/4045; G01N 27/48; G01N 33/0014;
        (Continued)

(56) References Cited

U.S. PATENT DOCUMENTS 2,269,459 A * 1/1942 Kleist ................... C03B 37/025
                                                                65/525
4,846,864 A * 7/1989 Huey ....................... D01D 5/24
                                                                65/439
                (Continued)

FOREIGN PATENT DOCUMENTS

CN        104937405 A        9/2015

OTHER PUBLICATIONS

Zhang et al., Rapid fabrication of high-aspect ratio platinum microprobes by electrochemical discharge etching, Materials, 2016, 9, 233 (Year: 2016).*
Tamizhanban et al., An automated pipette puller for fabrication of glass micropipettes, Rev. Sci. Instrum., 2014, 85, 055105 (Year: 2014).*

(Continued)

*Primary Examiner* — Shizhi Qian
(74) *Attorney, Agent, or Firm* — Cooper Legal Group, LLC

(57)                ABSTRACT
A microsensor for monitoring phosphine and a preparation method thereof are provided, where the microsensor includes an interfering substance removal module, used to remove other impurity gases and keep a phosphine gas; a phosphine signal measuring module, used for measuring a concentration of the phosphine gas; a guard electrode, used to consume excess phosphine gas in the microsensor; and a power supply module, used for supplying power to the phosphine signal measuring module and the guard electrode; the power supply module is respectively connected with the phosphine signal measuring module and the guard electrode; and the interfering substance removal module is located at a front end of the guard electrode.

3 Claims, 3 Drawing Sheets

(51) Int. Cl.
| | |
|---|---|
| *C25D 3/48* | (2006.01) |
| *C25D 7/06* | (2006.01) |
| *C25F 3/14* | (2006.01) |
| *G01N 27/416* | (2006.01) |
| *G01N 33/00* | (2006.01) |

(52) U.S. Cl.
CPC .............. *C25D 7/0607* (2013.01); *C25F 3/14*
(2013.01); *G01N 27/416* (2013.01); *G01N*
*33/0014* (2013.01)

(58) Field of Classification Search
CPC ..... C03B 37/0256; C03B 23/099; C25D 3/48;
C25D 7/0607; C25F 3/14; B01D 53/1468;
B01D 53/1487; B01D 53/14
See application file for complete search history.

(56) References Cited

U.S. PATENT DOCUMENTS

| | | | | |
|---|---|---|---|---|
| 5,997,706 | A * | 12/1999 | Kiesele .............. | G01N 27/4045 |
| | | | | 204/415 |
| 2015/0338370 | A1 * | 11/2015 | Larsen .............. | G01N 27/4045 |
| | | | | 73/31.05 |

OTHER PUBLICATIONS

Ono-Ogasawara et al., Determination of phosphine by adsorption sampling with modified silica gel and colorimetry of phosphate, Industrial Health, 1990, 28, 175-184 (Year: 1990).*

Roels et al., Determination of phosphine in biogas and sludge at ppt-levels with gas chromatography thermionic specific detection, Journal of Chromatography A, 2002, 952, 229-237 (Year: 2002).*

Andersen et al., An oxygen insensitive microsensor for nitrous oxide, Sensors and Actuators B, 2001, 81, 42-48 (Year: 2001).*

Author unknown, "A H2S microsensor forprofiling biofilms and sediments: Application in an acidic lake sediment" Aquatic Microbial Ecology, Jul. 1998, 10 pages.

Jeroschewski, et al. "An Amperometric Microsensor for the Determination of H2S in Aquatic Environments" Anal. Chem. 1996, 68, 4351-4357.

Author Unknown, "An oxygen microsensor with a guard cathode" Limnol. Oceanogr., 34(2). 1989, 474-478.

Nielsen et al. "Hydrogen microsensors with hydrogen sulfide traps" Sensors and Actuators B 215 (2015) 1-8.

Nakano, et al. "Preparation of thin gold-film electrode for an electrochemical gas sensor for phosphine and arsine" Sensors and Actuators B 21 (1994) 51-55.

* cited by examiner

E1: protective electrode

E2: reference electrode

E3: electrode outer shell

E4: working electrode

E5: protective sleeve

E6: permeable layer

First gas diffusion membrane

Second gas diffusion membrane

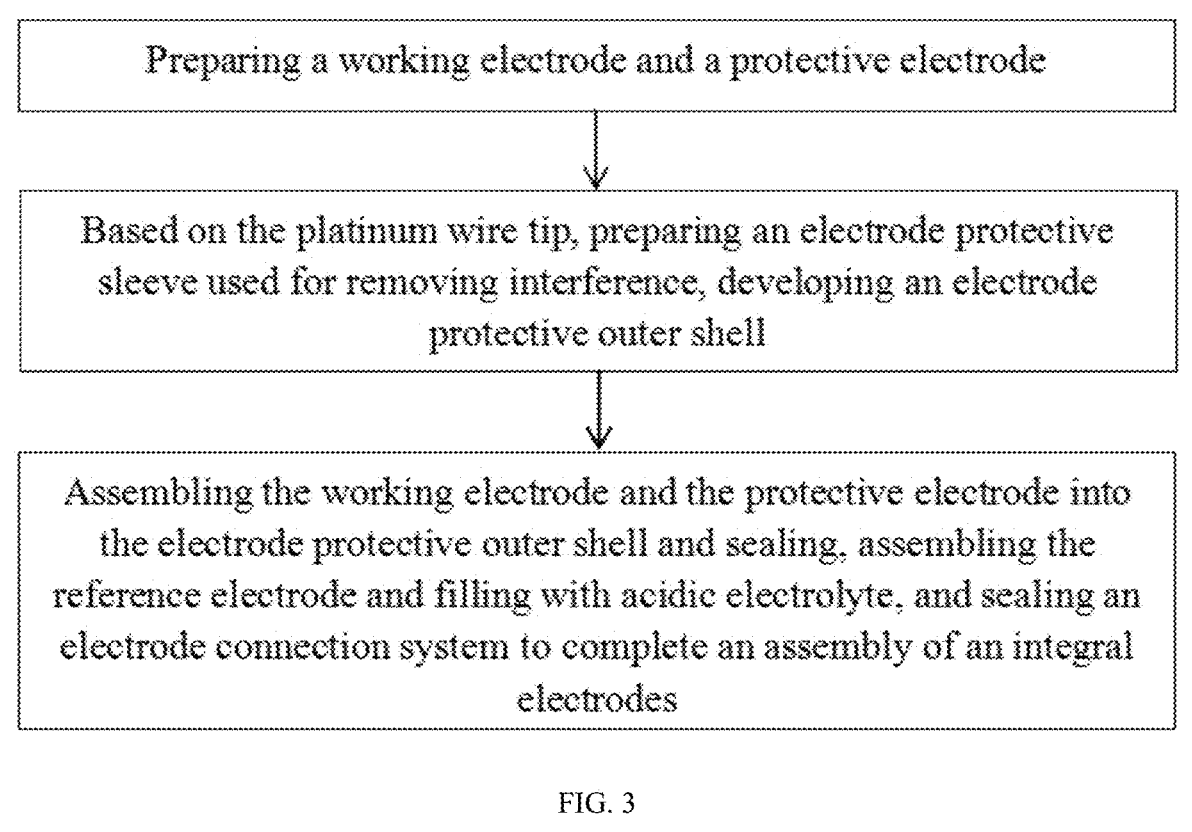

Preparing a working electrode and a protective electrode

Based on the platinum wire tip, preparing an electrode protective sleeve used for removing interference, developing an electrode protective outer shell Assembling the working electrode and the protective electrode into the electrode protective outer shell and sealing, assembling the reference electrode and filling with acidic electrolyte, and sealing an electrode connection system to complete an assembly of an integral electrodes

FIG. 3

MICROSENSOR FOR MONITORING PHOSPHINE AND PREPARATION METHOD THEREOF

CROSS-REFERENCE TO RELATED APPLICATIONS

This application claims priority to Chinese Patent Application No. 202210818509.1, filed on Jul. 12, 2022, the contents of which are hereby incorporated by reference.

TECHNICAL FIELD

The present application relates to the technical field of electrochemical microsensors, and in particular to a microsensor for monitoring phosphine and a preparation method thereof.

BACKGROUND

Phosphine is a colorless, highly toxic and flammable gas, mainly produced in the processes of fumigation and insecticide spraying in grain warehouses, sodium hypophosphite production, yellow phosphorus production and sludge precipitation and in the semiconductor industry, etc. Phosphine gas is highly toxic and can be smelled at a concentration of 2 to 4 milligrams per cubic metre ($mg/m^3$) in the air; it is poisonous at a concentration of more than 9.7 $mg/m^3$ in the air; it kills people at a concentration of 550 to 30 $mg/m^3$ in the air within 0.5 to 1.0 hours after exposure; and it kills people very quickly at a concentration of more than 2,798 $mg/m^3$ in the air. To prevent environmental pollution and biological poisoning by mixtures containing phosphine gas, it is necessary to monitor the concentrations of emissions and generation so as to give early warning.

In the natural environment, the concentration of phosphine ranges mainly from nanomolar to micromolar levels (parts per billion (ppb) level and below), which is lower than the above-mentioned artificially prescribed concentration ranges, making it difficult to achieve on-site monitoring of trace concentrations. At present, the major drawbacks of the devices for phosphine monitoring in the prior art are their large size (about 2×2×2 centimeters (cm)) and poor sensitivity (parts per million (ppm) level, with serious divergence below this concentration), mainly for man-made places such as grain warehouses and workshops with high discharge, and not for natural places such as waters, soils and gases with a lower concentration. The problems caused by such drawbacks are: ① destructive effects of sensors with large bulk on samples when used to monitor environmental media in a natural background, destroying phosphine samples that are already at low concentrations and sensitive to oxygen; ② still suboptimal detection limits even at ppb and ppm levels, and a low degree of overlap with concentrations of natural environmental background, making it difficult to be used for environmental monitoring in a natural context; and ③ poor anti-interference ability, for reductive gases such as sulfide, hydrogen, methane, carbon monoxide, etc. exist in the air at the same time are able to produce greater interference with conventional large sensors, or even with no selectivity at all.

SUMMARY

The present application aims at solving the problems existing in the prior art, and provides a microsensor for monitoring phosphine and a preparation method thereof, applicable to environmental monitoring systems.

To achieve the above objectives, the present application provides following technical schemes:

a microsensor for monitoring phosphine, including:

an interfering substance removal module, used to remove other impurity gases and keep a phosphine gas;

a phosphine signal measuring module, used for measuring a concentration of the phosphine gas;

a guard electrode, used to consume excess phosphine gas in the microsensor; and avoid the interferences from excess phosphine and reaction intermediates (HPO etc.)

a power supply module, used for supplying power to the phosphine signal measuring module and the guard electrode;

the power supply module is respectively connected with the phosphine signal measuring module and the guard electrode; and the interfering substance removal module is located at a front end of the guard electrode.

Optionally, the phosphine signal measuring module includes the guard electrode, a working electrode, a reference electrode, a second gas diffusion membrane and an electrode outer shell, where the guard electrode, the reference electrode, the working electrode and the second gas diffusion membrane are all placed inside the electrode outer shell, and the second gas diffusion membrane is placed at a bottom of the electrode outer shell.

Optionally, the phosphine signal measuring module further includes an external stabilized high-precision power supply and an ammeter, and the reference electrode and the working electrode are respectively connected in series with the external stabilized high-precision power supply and the ammeter; the reference electrode and the guard electrode are connected in series with the stabilized high-precision power supply.

Optionally, a process of the phosphine signal measuring module measuring a phosphine signal includes: using the stabilized high-precision power supply to provide a polarization voltage, allowing a polarization reaction on a surface of the working electrode based on the polarization voltage provided, generating a polarization current signal, and measuring the polarization current signal by the ammeter to obtain the phosphine signal.

Optionally, the interfering substance removal module includes a protective sleeve, a first gas diffusion membrane and a shell, where the protective sleeve is filled with an alkaline salt solution, the first gas diffusion membrane is configured at a bottom of the shell for filtering out other impurity gases; and the protective sleeve constitutes a glass tube with liquid sealed inside.

To achieve the above objectives, the present application also provides a method for preparing a detective element of the microsensor for monitoring phosphine, including following steps:

preparing a working electrode and a guard electrode, where the working electrode includes a platinum wire tip and a tail end;

preparing an electrode protective sleeve based on the platinum wire tip, developing an electrode protective outer shell; and assembling the working electrode and the guard electrode into the electrode protective outer shell and sealing, assembling the reference electrode and filling with acidic electrolyte, and sealing an electrode connection system to complete an assembly of the detective element.

Optionally, a process of preparing the working electrode includes:

drawing a glass into a hollow glass filament; electrochemically ablate a platinum wire until one end of the platinum wire is ablated into a micron-sized platinum wire tip, penetrating the micron-sized platinum wire tip into the hollow glass filament, with platinum wire tip and platinum wire tail exposed, then hot-melting and sealing the hollow glass filament.

Optionally, a surface of the platinum wire tip is plated with gold to form a micron-thick gold coating.

Optionally, a process of preparing the electrode protective sleeve includes:

drawing a high-impedance glass tube with a diameter into the electrode protective outer shell with a tip of a micron diameter, filling the tip with silica gel to form a permeable layer; where a glass tube containing an alkaline solution is sleeved outside the tip to filter off other impurity gases and prevent the impurity gases from interfering with the microsensor.

The present application has the beneficial effects that:

the microsensor for monitoring phosphine and preparation method of the present application is highly selective against phosphine, insensitive to hydrogen, hydrogen sulfide, methane, carbon monoxide and other gases in the soil and sediment environment, and insensitive to changes of pH, salinity and agitation;

the microsensor of the present application is 3-6 orders of magnitude more sensitive than conventional sensors, reaching 5 nanomoles per liter, and is capable of being used to monitor phosphine in the environmental background; and the device of the present application is capable of continuous operation for more than six months, and the diameter of the sensitivity of the detective element is in the micron scale, with no damage to the measured soil, sediment and biological samples.

BRIEF DESCRIPTION OF THE DRAWINGS

For a clearer description of the technical schemes in the embodiments or prior art of the present application, the following drawings are briefly described for use in the embodiments, and it is obvious that the drawings in the following description are only some embodiments of the present application, and that other drawings are available to a person of ordinary skill in the art without creative labor.

FIG. 3 shows a process of a method for preparing a detective element of the microsensor for monitoring phosphine according to the present application.

DETAILED DESCRIPTION OF THE EMBODIMENTS

The technical schemes in the embodiments of the present application are described clearly and comprehensively below in conjunction with the accompanying drawings in the embodiments of the present application. Obviously, the described embodiments are only a part of the embodiments of the present application, and not all of them. Based on the embodiments in the present application, all other embodiments obtained by a person of ordinary skill in the art without making creative labor fall within the scope of protection of the present application.

To make the above-mentioned objectives, features and advantages of the present application more obvious and understandable, the present application is described in further detail below in conjunction with the accompanying drawings and specific embodiments.

Figure 1:
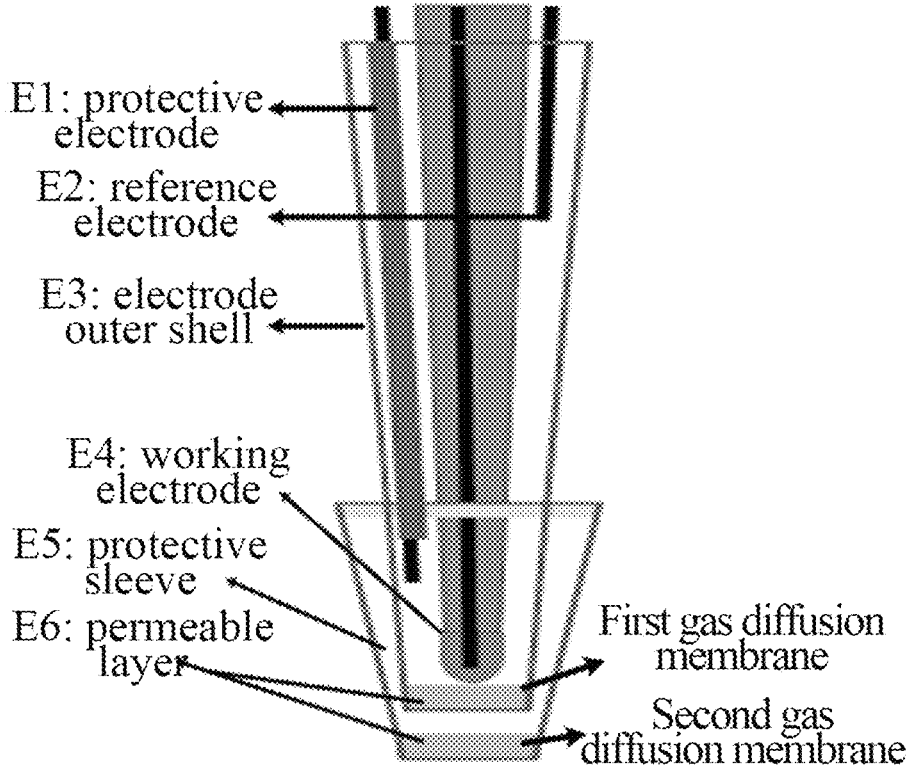
FIG. 1 is a schematic structural diagram of a microsensor according to an embodiment of the present application.

As shown in FIG. 1, this embodiment provides a microsensor for monitoring phosphine, including:

a gaseous membrane diffusion module, permeating only gases, including a first gas diffusion membrane and a second gas diffusion membrane;

an interfering substance removal module, used to remove other impurity gases and keep a phosphine gas;

a phosphine signal measuring module, used for measuring a concentration of the phosphine gas;

a guard electrode, used to consume excess phosphine gas in the microsensor; and an external power module, used to supply power to each module;

the external power supply module is respectively connected with the phosphine signal measuring module and the guard electrode; the first gas diffusion membrane is located at a tip of the interfering substance removal module, and the second gas diffusion membrane is located near a tip of the working electrode.

The gaseous membrane diffusion module allows phosphine gas to cross, but liquids and solids are not capable of penetrating the permeable membrane.

The interfering substance removal module is located between two gas diffusion membranes.

Figure 2:
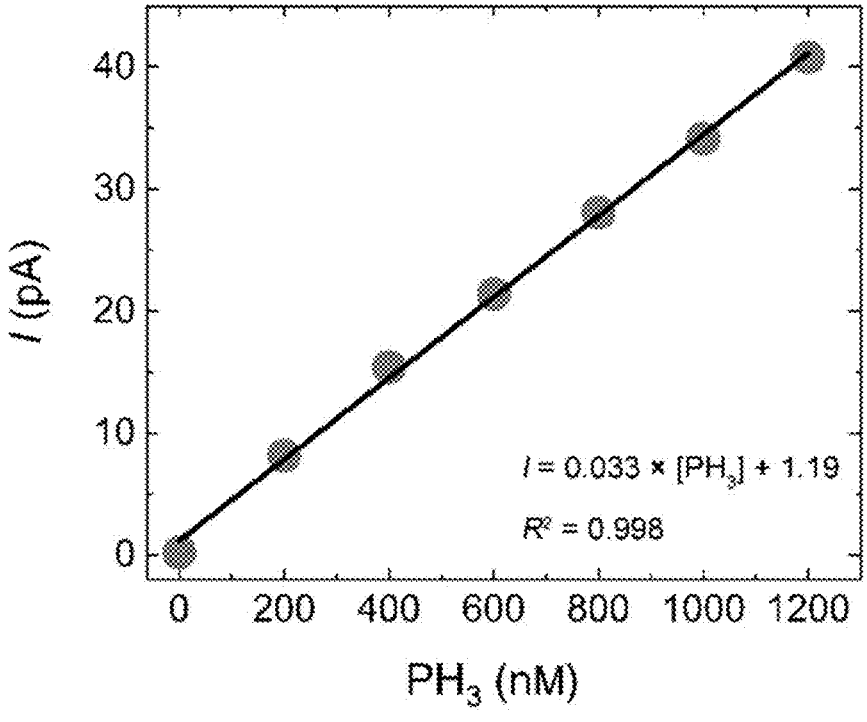
FIG. 2 shows a standard curve of the microsensor in seawater according to an embodiment of the present application.

The phosphine signal measuring module constitutes a reference electrode E2 and a working electrode E4 connected in series with a self-developed high-precision power supply and a high-precision ammeter. The power supply provides a polarization voltage, and phosphine is polarized on a surface of the working electrode to generate a polarization current signal stronger than a background value, which is captured by the ammeter connected in series; the signal is positively proportional to the concentration, and a measurement curve is derived as shown in FIG. 2.

The guard electrode-reference electrode circuit involves the reference electrode E2 and a guard electrode E1 connected in series with same power supply as described above, with both ends providing only the same polarization voltage as that of two ends of the phosphine signal measuring module, and no signal of the polarization current is collected for the sole purpose of consuming excess phosphine in a measurement system.

The present application relates to a method for preparing a detective element of the microsensor for monitoring phosphine, including following steps as shown in FIG. 3:

preparing a working electrode and a guard electrode, where the working electrode includes a platinum wire tip and a tail end;

based on the platinum wire tip, preparing an electrode protective sleeve used for removing interference, developing an electrode protective outer shell; and assembling the working electrode and the guard electrode into the electrode protective outer shell and sealing, assembling the reference electrode and filling with acidic electrolyte, and sealing an electrode connection system to complete an assembly of an integral electrodes.

Preparation of the working electrode E4 is as follows:

step 1, drawing a glass with high impedance and stability and millimeter diameter into a hollow glass filament;

step 2, ablating one end of a high-purity platinum wire into a platinum wire tip with a micron diameter;

step 3, penetrating the platinum wire into the hollow glass filament, with platinum wire tip and platinum wire tail exposed, and hot-melting a middle and sealing for later use; and step 4, plating the platinum wire tip with gold to form a gold coating.

Preparation of guard electrode E1 is as follows:

The steps are the same as the preparation of the working electrode.

Preparation of electrode protective sleeve E5:

step 1, drawing a high-impedance glass tube with a diameter into the electrode protective outer shell of the microsensor with a tip of a micron diameter; and step 2, filling the tip with silica gel to form a second gas diffusion layer, i.e. the permeable layer.

Integral electrode assembly (FIG. 1):

step 1, drawing a high-impedance glass tube into an electrode outer shell with a tip of a micron diameter;

step 2, sealing and filling silica gel at an outlet of the electrode outer shell;

step 3, assembling the working electrode into the electrode outer shell with a tip close to the first gas diffusion membrane;

step 4, assembling the guard electrode to the silica gel layer of the electrode outer shell;

step 5, assembling a reference electrode E2;

step 6, filling electrolyte;

step 7, using an electromagnetically insulated cable to connect the reference electrode, the working electrode, and the guard electrode, respectively;

step 8, sealing an electrode connection system with sealant; and step 9, adding a protective sleeve filled with filter solution to an inner tip of the electrode.

The interface in contact with the external environment in the microsensor is a silica gel gas diffusion membrane (E6). The electrolyte uses a mixed solution of strong acid salt to suppress the interference of hydrogen in the ambient background. The surface of the working electrode platinum wire is plated with gold to increase the sensitivity and selectivity of the electrode to phosphine and further exclude the interference of methane and hydrogen. The process of enveloping the glass tube by drawing allows the electrode tip with a diameter of micron to minimize the damage of the microsensor to the sample.

A glass tube containing an alkaline salt solution is sleeved on the outside of the tip of the microsensor, and a gas permeable membrane (E6) manufactured using the same process is used at the tip of the protective sleeve to reduce the interference of other gases with the microsensor.

The microsensor for monitoring phosphine and preparation method of the present application is highly selective against phosphine, insensitive to hydrogen, hydrogen sulfide, methane, carbon monoxide and other gases in the soil and sediment environment, and insensitive to changes of pH, salinity and agitation; the microsensor of the present application is 3-6 orders of magnitude more sensitive than conventional sensors, reaching 5 nanomoles per liter, and is capable of being used to monitor phosphine in the environmental background; and the device of the present application is capable of continuous operation for more than six months, and the diameter of the sensitivity of the detective element is in the micron scale, with no damage to the measured soil, sediment and biological samples.

The above described embodiments represent only a description of the preferred way of the present application, not a limitation of the scope of the present application. Without departing from the spirit of the design of the present application, all kinds of deformations and improvements made to the technical schemes of the present application by a person of ordinary skill in the art shall fall within the scope of protection determined by the claims of the present application.

What is claimed is:

1. A method for preparing a detective element of a microsensor for monitoring phosphine, comprising:

preparing a working electrode and a guard electrode, wherein the working electrode comprises a micron-sized platinum wire tip and a platinum wire tail end;

preparing an electrode protective sleeve based on the micron-sized platinum wire tip;

developing an electrode protective outer shell;

assembling the working electrode and the guard electrode into the electrode protective outer shell and sealing the electrode protective outer shell;

assembling a reference electrode and filling with acidic electrolyte; and sealing an electrode connection system to complete an assembly of the detective element, wherein the process of preparing the electrode protective sleeve comprises:

drawing a glass tube with a diameter into the electrode protective outer shell with a tip of a micron diameter; and filling the tip with silica gel to form a permeable layer;

wherein the glass tube containing an alkaline solution is sleeved outside the tip to remove impurity gases and allow the phosphine to cross such that the microsensor is selective against the phosphine, insensitive to hydrogen, hydrogen sulfide, methane, and carbon monoxide in soil and sediment environment.

2. The method for preparing the detective element of the microsensor for monitoring phosphine according to claim 1, wherein the process of preparing the working electrode comprises:

drawing a glass into a hollow glass filament;

electrochemically ablating a platinum wire until one end of the platinum wire is ablated into the micron-sized platinum wire tip; and penetrating the micron-sized platinum wire tip into the hollow glass filament, with the micron-sized platinum wire tip and the platinum wire tail end exposed, then hot-melting and sealing the hollow glass filament.

3. The method for preparing the detective element of the microsensor for monitoring phosphine according to claim 2, wherein a surface of the micron-sized platinum wire tip is plated with gold to form a micron-thick gold coating.

* * * * *